(12) United States Patent
Davison et al.

(10) Patent No.: US 6,387,109 B1
(45) Date of Patent: *May 14, 2002

(54) METHODS AND DEVICE FOR IMPROVING BLOOD FLOW TO HEART OF A PATIENT

(75) Inventors: Thomas W. Davison, North Attleboro; Stephen DiMatteo, Seehonk, both of MA (US)

(73) Assignee: Ethicon Endo-Surgery, Inc., Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/365,639

(22) Filed: Aug. 3, 1999

Related U.S. Application Data

(60) Division of application No. 08/770,319, filed on Dec. 20, 1996, now Pat. No. 5,989,274, which is a continuation-in-part of application No. 08/733,128, filed on Oct. 17, 1996, now abandoned.

(51) Int. Cl.[7] .............................................. A61B 17/32
(52) U.S. Cl. ........................................ 606/169; 604/22
(58) Field of Search ................................ 606/167, 169, 606/170, 108, 1.94, 159, 7, 15; 604/22; 601/2, 4

(56) References Cited

U.S. PATENT DOCUMENTS

| 2,874,470 A | 2/1959 | Richards ......................... 32/58 |
| 3,075,288 A | 1/1963 | Balamuth et al. ............... 32/58 |
| 3,076,904 A | 2/1963 | Kleesattel et al. ............. 310/26 |
| 3,213,537 A | 10/1965 | Balamuth et al. ............... 32/28 |
| 3,352,303 A | 11/1967 | Delaney ....................... 128/24 |
| 3,368,280 A | 2/1968 | Fridman et al. ................ 32/58 |
| 3,375,583 A | 4/1968 | Blank et al. .................... 32/26 |
| 3,433,226 A | 3/1969 | Boyd .......................... 128/305 |

(List continued on next page.)

FOREIGN PATENT DOCUMENTS

| CA | 1098003 | 9/1977 |
| DE | 29 22 239 | 5/1979 |
| DE | 37 07 921 A1 | 3/1987 |

(List continued on next page.)

OTHER PUBLICATIONS

UltraCision Incorporated, The Harmonic Scalpel® For Gynecological Surgery, Product Sheet, 9/92.
UltraCision Incorporated, The Harmonic Scalpel® For General Surgery, Product Sheet, 1/93.
Snowden–Pencer, Inc., Endoscopic Plastic Surgery, 1993.
UltraCision Incorporated, Harmonic Scalpel® Price List, 1995.

(List continued on next page.)

*Primary Examiner*—Kevin Truong
(74) *Attorney, Agent, or Firm*—Verne E. Kreger, Jr.

(57) ABSTRACT

One device in accordance with the present invention includes a surgical device for creating channels in tissue of a patient. The device includes a catheter defining a lumen and a transducer assembly carried by the catheter along a lengthwise dimension of the catheter. An end effector is operatively coupled to the transducer assembly and extends distally relative to the transducer assembly. The end effector has a vibrating channel-forming tip wherein the channel-forming tip is adapted to create channels in the heart of a patient. A method in accordance with the present invention includes the steps of inserting an end effector having a tip into a patient, placing the tip of the end effector in direct contact with a surface of the heart, energizing the end effector to cause the tip to vibrate, piercing through the surface of the heart with the tip to create a channel, and removing the end effector.

13 Claims, 4 Drawing Sheets

U.S. PATENT DOCUMENTS

| | | | | |
|---|---|---|---|---|
| 3,488,851 A | | 1/1970 | Haydu | 32/58 |
| 3,489,930 A | | 1/1970 | Shoh | 310/8.1 |
| 3,518,766 A | | 7/1970 | Burt | 32/58 |
| 3,526,036 A | | 9/1970 | Goof | 32/28 |
| 3,526,792 A | | 9/1970 | Shoh | 310/8.1 |
| 3,589,012 A | | 6/1971 | Richman | 32/58 |
| 3,589,363 A | | 6/1971 | Banko et al. | 128/276 |
| 3,593,425 A | | 7/1971 | Robinson | 32/58 |
| 3,636,947 A | | 1/1972 | Balamuth | 128/66 |
| 3,645,255 A | | 2/1972 | Robinson | 128/24 A |
| 3,654,502 A | | 4/1972 | Carmona et al. | 310/26 |
| 3,654,540 A | | 4/1972 | Honig et al. | 318/118 |
| 3,703,037 A | | 11/1972 | Robinson | 32/58 |
| 3,809,977 A | | 5/1974 | Balamuth et al. | 318/116 |
| 3,930,173 A | | 12/1975 | Banko | 310/26 |
| 3,956,826 A | | 5/1976 | Perdreaux, Jr. | 32/58 |
| 4,156,157 A | | 5/1979 | Mabille | 310/316 |
| 4,169,984 A | | 10/1979 | Parisi | 310/323 |
| 4,175,242 A | | 11/1979 | Kleinschmidt | 310/316 |
| 4,188,952 A | | 2/1980 | Loschilov et al. | 128/305 |
| 4,223,676 A | | 9/1980 | Wuchinich et al. | 128/276 |
| 4,227,110 A | | 10/1980 | Douglas et al. | 310/316 |
| RE30,536 E | | 3/1981 | Perdreaux, Jr. | 433/86 |
| 4,370,131 A | | 1/1983 | Banko | 433/86 |
| 4,371,816 A | | 2/1983 | Wieser | 318/116 |
| 4,406,284 A | | 9/1983 | Banko | 128/303 |
| 4,491,132 A | | 1/1985 | Aikins | 128/305 |
| 4,492,574 A | | 1/1985 | Warrin et al. | 433/81 |
| 4,658,817 A | | 4/1987 | Hardy | 128/303.1 |
| 4,676,231 A | | 6/1987 | Hisazumi et al. | 128/6 |
| 4,693,556 A | | 9/1987 | McCaughan, Jr. | 350/320 |
| 4,750,488 A | | 6/1988 | Wuchinich et al. | 128/303 |
| 4,808,153 A | | 2/1989 | Parisi | 604/22 |
| 4,816,018 A | | 3/1989 | Parisi | 604/22 |
| 4,820,152 A | | 4/1989 | Warrin et al. | 433/83 |
| 4,867,141 A | | 9/1989 | Nakada et al. | 128/24 |
| 4,870,953 A | | 10/1989 | DonMicheal et al. | 128/24 |
| 4,883,458 A | | 11/1989 | Shiber | 604/22 |
| 4,890,898 A | | 1/1990 | Bentley et al. | 350/96.23 |
| 4,897,079 A | | 1/1990 | Zaleski et al. | 604/22 |
| 4,920,954 A | | 5/1990 | Alliger et al. | 128/24 |
| 4,922,902 A | | 5/1990 | Wuchinich et al. | 604/22 |
| 4,931,047 A | | 6/1990 | Broadwin et al. | 604/22 |
| 4,936,281 A | * | 6/1990 | Stasz | 606/169 |
| 4,962,755 A | | 10/1990 | King et al. | 128/24 |
| 4,974,162 A | | 11/1990 | Siegel et al. | 364/413.06 |
| 4,974,590 A | | 12/1990 | Saito | 128/662.06 |
| 4,979,952 A | | 12/1990 | Kubota et al. | 606/169 |
| 4,997,431 A | | 3/1991 | Isner et al. | 606/15 |
| 5,011,471 A | | 4/1991 | Miyazaki et al. | 604/22 |
| 5,026,387 A | | 6/1991 | Thomas | 606/169 |
| 5,047,043 A | | 9/1991 | Kubota et al. | 606/169 |
| 5,057,119 A | | 10/1991 | Clark et al. | 606/169 |
| 5,059,210 A | | 10/1991 | Clark et al. | 606/169 |
| 5,069,664 A | | 12/1991 | Guess et al. | 604/22 |
| 5,091,404 A | | 2/1992 | Elgebaly | 514/401 |
| 5,106,386 A | | 4/1992 | Isner et al. | 606/15 |
| 5,112,300 A | | 5/1992 | Ureche | 604/22 |
| 5,123,903 A | | 6/1992 | Quaid et al. | 604/22 |
| 5,125,924 A | | 6/1992 | Rudko | 606/12 |
| 5,125,926 A | | 6/1992 | Rudko et al. | 606/19 |
| 5,151,084 A | | 9/1992 | Khek | 604/22 |
| 5,151,085 A | | 9/1992 | Sakurai et al. | 604/22 |
| 5,160,317 A | | 11/1992 | Costin | 604/22 |
| 5,167,725 A | | 12/1992 | Clark et al. | 428/680 |
| 5,180,383 A | | 1/1993 | Idemoto et al. | 202/32 |
| 5,190,517 A | | 3/1993 | Zieve et al. | 604/22 |
| 5,231,086 A | | 7/1993 | Sollevi | 514/46 |
| 5,244,460 A | | 9/1993 | Unger et al. | 604/53 |
| 5,248,296 A | | 9/1993 | Alliger | 609/22 |
| 5,263,957 A | | 11/1993 | Davison | 606/169 |
| 5,269,291 A | * | 12/1993 | Carter | 606/169 |
| 5,269,309 A | | 12/1993 | Fort et al. | 128/661.01 |
| 5,304,115 A | * | 4/1994 | Pflueger et al. | 606/169 |
| 5,322,055 A | | 6/1994 | Davison et al. | 601/2 |
| 5,324,299 A | | 6/1994 | Davison et al. | 606/167 |
| 5,342,292 A | | 8/1994 | Nita et al. | 604/22 |
| 5,344,420 A | | 9/1994 | Hilal et al. | 606/28 |
| 5,346,502 A | | 9/1994 | Estabrook et al. | 606/169 |
| 5,380,274 A | | 1/1995 | Nita | 604/22 |
| 5,380,316 A | | 1/1995 | Aita et al. | 606/7 |
| 5,382,162 A | | 1/1995 | Sharp | 433/116 |
| 5,389,096 A | | 2/1995 | Aita et al. | 606/7 |
| 5,397,269 A | | 3/1995 | Beaty et al. | 464/38 |
| 5,413,107 A | | 5/1995 | Oakley et al. | 128/662.06 |
| 5,417,672 A | | 5/1995 | Nita et al. | 604/283 |
| 5,425,704 A | | 6/1995 | Sakurai et al. | 604/22 |
| 5,427,118 A | * | 6/1995 | Nita et al. | 604/22 |
| 5,438,554 A | | 8/1995 | Seyed-Bolorforosh et al. | 367/140 |
| 5,449,370 A | | 9/1995 | Vaitekunas | 606/169 |
| 5,451,220 A | * | 9/1995 | Ciervo | 606/169 |
| 5,452,733 A | | 9/1995 | Sterman et al. | 128/898 |
| 5,472,447 A | | 12/1995 | Abrams et al. | 606/169 |
| 5,474,530 A | * | 12/1995 | Passafaro et al. | 606/169 |
| 5,501,228 A | | 3/1996 | Lafontaine et al. | 128/692 |
| 5,503,150 A | | 4/1996 | Evans | 128/653.1 |
| 5,507,738 A | | 4/1996 | Ciervo | 606/1 |
| 5,507,743 A | | 4/1996 | Edwards et al. | 606/41 |
| 5,509,916 A | | 4/1996 | Taylor | 606/13 |
| 5,526,815 A | | 6/1996 | Granz et al. | 128/660.03 |
| 5,540,656 A | | 7/1996 | Pflueger et al. | 604/22 |
| 5,542,917 A | | 8/1996 | Nita et al. | 604/22 |
| 5,546,947 A | | 8/1996 | Yagami et al. | 128/662.06 |
| 5,554,152 A | | 9/1996 | Aita et al. | 606/7 |
| 5,562,609 A | | 10/1996 | Brumbach | 604/22 |
| 5,562,610 A | | 10/1996 | Brumbach | 604/22 |
| 5,582,588 A | * | 12/1996 | Sakurai et al. | 604/22 |
| 5,606,974 A | | 3/1997 | Castellano et al. | 128/662.06 |
| 5,628,743 A | | 5/1997 | Cimino | 606/1 |
| 5,634,466 A | | 6/1997 | Gruner | 128/662.06 |
| 5,713,848 A | * | 2/1998 | Dubrul et al. | 604/22 |
| 5,746,756 A | * | 5/1998 | Bromfield et al. | 606/169 |

FOREIGN PATENT DOCUMENTS

| | | |
|---|---|---|
| EP | 0 495 634 A2 | 1/1992 |
| EP | 0 624 346 A3 | 5/1994 |
| EP | 0 624 346 A2 | 5/1994 |
| JP | 56-38931 | 4/1981 |
| JP | 56-108085 | 8/1981 |
| JP | 61-265136 | 11/1986 |
| JP | 2-99049 | 4/1990 |
| RU | 1388002 A1 | 4/1988 |
| WO | WO 91/13591 | 3/1991 |
| WO | WO 92/02658 | 7/1991 |
| WO | 0 495 634 A3 | 1/1992 |
| WO | WO 92/14514 | 2/1992 |
| WO | WO 93/14708 | 1/1993 |
| WO | WO 93/16646 | 1/1993 |
| WO | WO 96/29935 | 4/1996 |
| WO | WO 96/34561 | 5/1996 |
| WO | WO 97/07735 | 8/1996 |

OTHER PUBLICATIONS

UltraCision Incorporated, Harmonic Scalpel® Operating Manual, 3/95.

Ethicon Endo–Surgery, Inc., Ultracision CS/LCS Layout Brochure, 1996.

Cooper LaserSonics, Inc., Ultrasonic Surgucal Aspirator NS–100 Operator Manual, 1984, pp. 12, 13, 16, 17, and 29–33.

Mirhoseini et al., "Lasers In Cardiothoracic Surgery", Chapter 21, pp. 216–232.

"Punching Holes in the Heart With Lasers Can Stave Off Attacks When Arteries Clog", The Wall Street Journal, Medicine.

United States Catheter & Instrument Corporation Price List for Radiopaque Desilets–Hoffman Catheter Introducer.

Mirhoseini, "Laser Revascularization Of The Heart", New Frontiers In Laser Medicine and Surgery, 296–303.

Mirhoseini et al., "Laser Myocardial Revascularization, Lasers in Surgery and Medcine", 459–461 (1986).

Mirhoseini, Medical Instrumentation, vol. 17, No. 6, 397–403 (Nov.–Dec. 1983).

Mirhoseini et al., "Myocardial Revascularization, By Laser", Lasers in Surgery and Medicine, 3:241,245 (1983).

Mirhoseini et al., "Transventricular Revascularization By Laser", Lasers in Surgery and Medicine, 187–198 (1982).

Mirhoseini et al., "Revascularization Of the Heart By Laser", Journal of Micrsurgery, 253–260 (Jun. 1981).

"Laser Surgery Revascularizes the Heart in Treatment of Ischemic Heart Disease", Cover News, Chirurgia International.

Jeevanandam et al., "Myocardial Revascularization By Laser–Induced Channels", Surgical Forum XLI, 225–227 (Oct. 1990).

Mirhoseini et al., "Clinical And Histological Evaluation Of Laser Myocardial Revascularization", Journal of Clinical Laser Medicine & Surgery, 73–78 (Jun. 1990).

Mirhoseini et al., "New Concepts In Revascularization Of The Myocardium", Ann. Thorac. Surg., 45:415–420 (Apr. 1988).

Mike Fillon, "A Kinder Cut", Popular Mechanics, 90–91, (Oct. 1996).

"PLC's Heart Laser Takes Over Center Stage", In Vivo, The Business and Medicine Report, 9–14, (Apr. 1995).

H.T. Aretz, "Intraluminal Ultrasound Guidance Of Transverse Laser Coronary Atherectomy", SPIE vol. 1201, Optical Fibers In Medicine V, 68–78, (1990).

Hardy et al., "Regional Myocardial Blood Flow And Cardian Mechanics In Dog Hearts With $CO_2$ Laser–Induced Intramyocardial Revascularization", Basic Res. Cardiol., vol. 85, No. 2, p. 179–196.

* cited by examiner

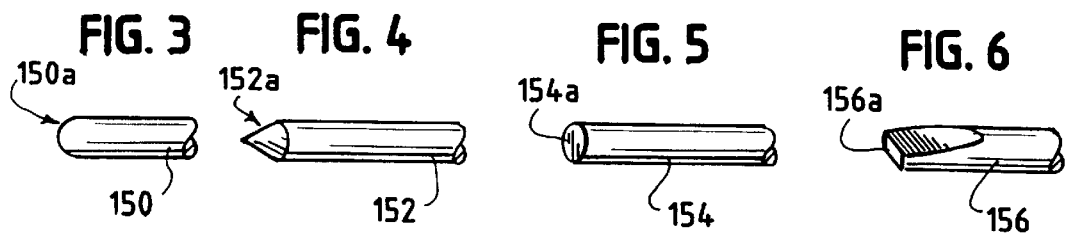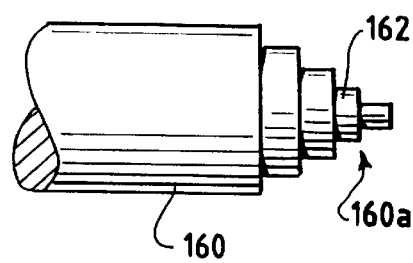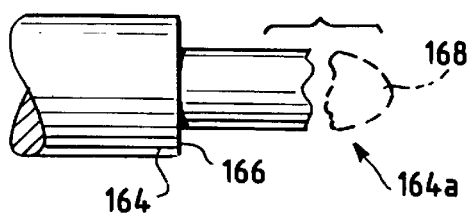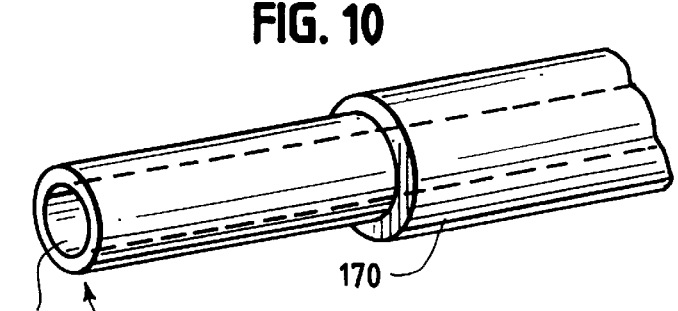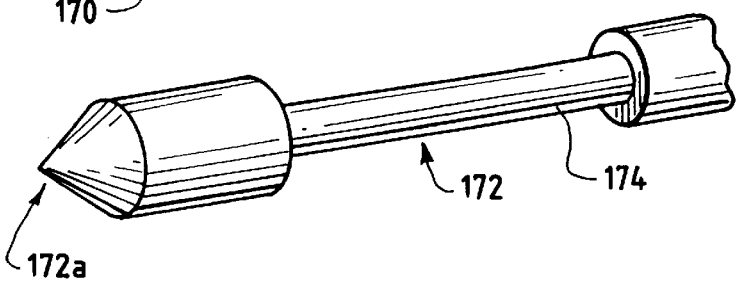

METHODS AND DEVICE FOR IMPROVING BLOOD FLOW TO HEART OF A PATIENT

RELATED APPLICATIONS

This is a Divisional of prior application No.: 08/770,319, filed Dec. 20, 1996 now U.S. Pat. No. 5,989,274.

This application is a continuation-in-part of application Ser. No. 08/733,128, filed on Oct. 17, 1996, now abandoned.

FIELD OF THE INVENTION

The present invention relates generally to surgical devices and procedures. More particularly, it relates to methods and devices to improve the flow of blood to the heart by transmyocardial revascularization.

BACKGROUND OF THE INVENTION

Heart disease presents a major concern in western societies. Heart disease may cause chest pains, strokes, heart attacks, or even death. One form of heart disease is ischemic heart disease, a condition where the heart or myocardium does not receive an adequate nutritive blood supply. Typically, this condition occurs when the coronary arteries become blocked by plaque build-up on their inner walls.

When the plaque build-up of the coronary arteries hinders the flow of blood to the heart, the heart may become starved for nutrition and oxygen. As a result, the tissue of the heart may scar, causing the heart to be weakened.

A number of approaches have been developed for treating heart disease. In less severe cases, proper diet and exercise may improve heart conditions. However, if diet and exercise are not effective, medication may be prescribed. If heart disease still persists, a minimally invasive or invasive procedure is usually performed.

There are several types of traditional medical procedures that may be used to improve blood supply to the heart. For example, coronary bypass surgery or percutaneous transluminal coronary angioplasty (PTCA) may be performed to increase blood flow to the heart.

Coronary bypass surgery involves open heart surgery where a surgeon removes a blood vessel from another part of the body, such as the leg or inside the chest wall, and uses the vessel to construct a detour around the blocked coronary artery. One end of the vessel is attached below the blockage while the other end is attached above the blockage. As a result, blood may flow around the obstruction into the heart.

However, because bypass surgery typically requires extensive and complicated surgery, the patient needs to have adequate lung and kidney function in order to tolerate such surgery. This procedure also requires postoperative care in an intensive care unit, seven to ten days in the hospital, and several months of recovery. Other complications, such as strokes, heart attacks, or infections, may develop during or as a consequence of the surgery. In addition, the blood vessel may close or become blocked several months after the surgery.

In PTCA, a surgeon inserts a thin wire through a small incision in an arm or leg artery of a patient and threads the wire toward the blocked area of the coronary artery. Next, a guide catheter may be passed over the wire and a balloon-tipped catheter is usually it threaded through the guide catheter. When the balloon-tipped catheter reaches the blockage area, the balloon is inflated to compress the plaque build-up against the coronary artery walls, widening the artery for blood flow. The balloon-tipped catheter may then be deflated and withdrawn from the patient.

If the artery closes or threatens to close, a balloon catheter having a mesh stent may be used. As the stented balloon inflates, the mesh of the stent expands and remains in place to hold the artery open after the balloon catheter has been removed.

More recently, Laser Transmyocardial Revascularization (LTR) has been used as an alterative to coronary bypass surgery or PTCA. This technique is used to supplement the blood supply received by the heart by providing the myocardium direct access to blood in the ventricle chamber. In one known approach, LTR is performed using a high power, pulsed, $CO_2$ laser. The laser may be operated to create a channel from the ventricle to the myocardium. The laser is fired against the outer ventricle surface of the heart when the ventricle is fall of blood. The blood in the ventricle acts as a backstop preventing the energy of the laser from penetrating through the other side of the ventricle or damaging nearby tissue. After a channel is formed, blood may flow through the resulting channel from the ventricle into the myocardium.

However, the cost of the laser is quite high, as is the cost of the procedure. The laser is ordinarily quite large and takes up significant space in the operating room. In addition, LTR is not always easily adaptable for thoracoscopic heart surgery and usually requires a 2.5 cm mini-thoracotomy. Furthermore, LTR ordinarily requires an EKG to synchronize the firing of the laser when the heart is fall of blood to absorb the laser beam.

Ultrasonic devices are also known for assisting a surgeon in cutting tissue. For example, U.S. Pat. No. 5,449,370 entitled "Blunt Tipped Ultrasonic Trocars," which is herein incorporated by reference, discloses a trocar to puncture an abdominal wall of a patient. U.S. Pat. No. 5,324,299 entitled "Ultrasonic Scalpel Blade And Method Of Application," which is incorporated herein by reference, discloses an ultrasonic device including a blade portion having a recess that defines a hook for grasping and tensioning loose tissue to facilitate cutting. U.S. Pat. No. 5,322,055 entitled "Clamp Coagulator/Cutting System For Ultrasonic Surgical Instruments," which is incorporated herein by reference, also discloses a surgical instrument for cutting tissue. The instrument includes an ultrasonic blade for use with a clamp to improve tissue cutting.

Accordingly, there is a need for devices and methods to treat heart disease. It would be beneficial to provide devices and methods to achieve a more effective treatment of heart disease. It would also be desirable to provide a cost-effective and minimally intrusive procedure to improve blood flow to the heart.

SUMMARY OF THE INVENTION

The present invention provides methods and devices to treat certain types of heart disease and to improve blood flow to tissue in a heart of a patient. The devices and methods of the present invention provide an efficient and minimally intrusive procedure to improve the blood supply to the myocardium of the heart. This is accomplished by a form of transmyocardial revascularization (TMR) where the heart is ultrasonically pierced to create a channel from the left ventricle to the myocardium.

The devices in accordance with the present invention can be inserted into the cardiovascular system of a patient and guided to the left ventricle of the heart. These devices create channels through the inner wall allowing blood to flow directly from the ventricle into the myocardium. The blood brings oxygen to the starved tissue.

One surgical device in accordance with the present invention includes a catheter defining a lumen. A transducer assembly is carried by the catheter along a lengthwise dimension of the catheter. An end effector is operatively coupled to the transducer assembly and extends distally relative to the transducer assembly. The end effector has a vibrating channel-forming tip wherein the channel-forming tip is adapted to create channels in the heart of a patient.

One method in accordance with the present invention includes the steps of inserting an end effector having a tip into a patient and placing the tip of the end effector in direct contact with a surface of the heart. The method also includes the steps of energizing the end effector to cause the tip to vibrate, and piercing through the surface of the heart with the tip to create a channel, and removing the end effector.

It is to be understood that both the foregoing general description and the following detailed description are exemplary and explanatory and are intended to provide further explanation of the invention as claimed.

The invention, together with further objects and attendant advantages, will best be understood by reference to the following detailed description of the presently preferred embodiment of the invention, taken in conjunction with the accompanying drawings.

BRIEF DESCRIPTION OF THE DRAWINGS

FIGS. 3–9 are fragmentary perspective views of preferred embodiments of an end effector of the surgical system of FIG. 2;

FIGS. 10–11 are fragmentary perspective views of other preferred embodiments of an end effector of an surgical system of FIG. 2;

DESCRIPTION OF THE PREFERRED EMBODIMENTS

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limitation.

Figure 1:
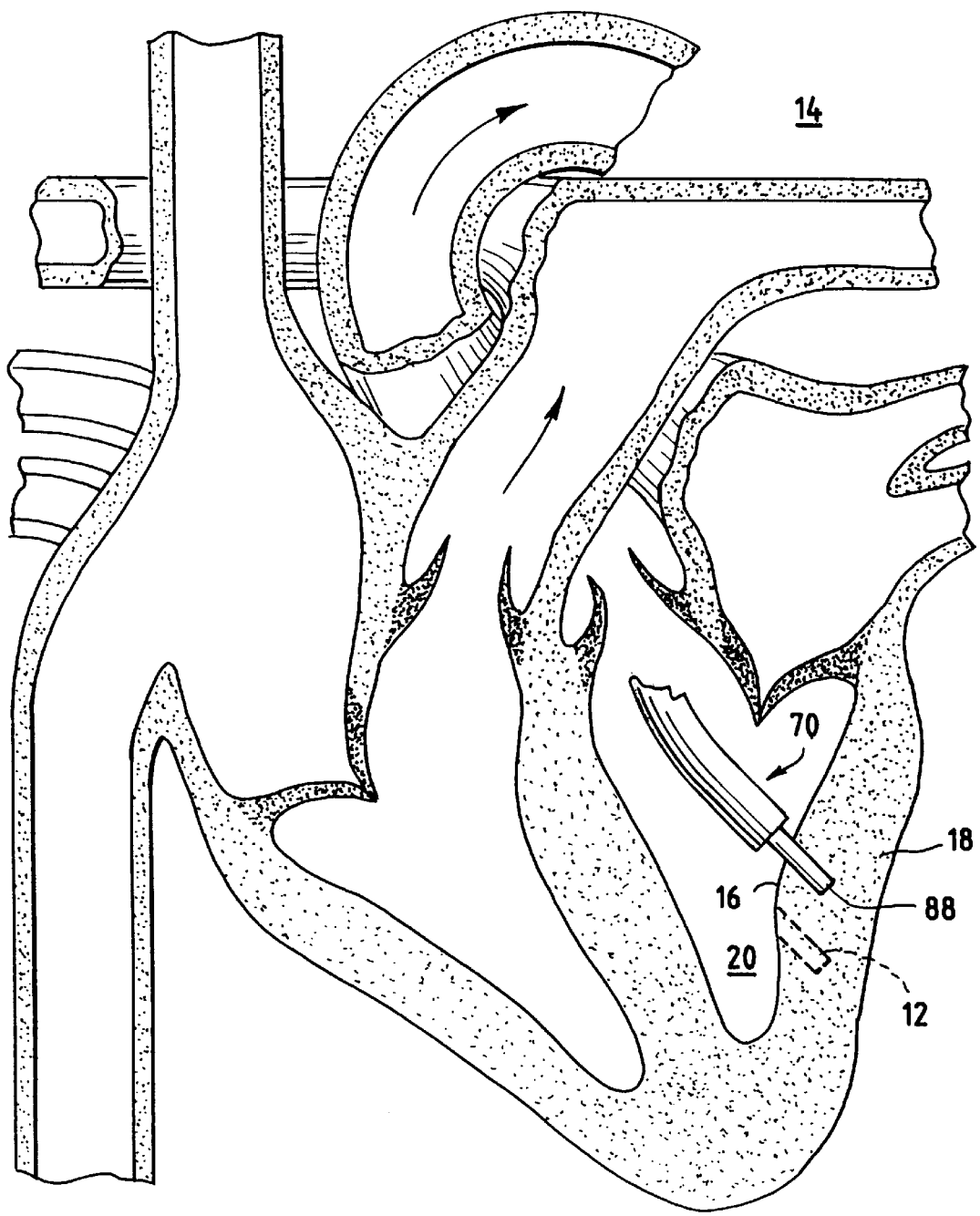
FIG. 1 is a partial diagrammatic view of one preferred embodiment of a probe assembly of an surgical system creating channels in a heart of a patient.

Referring now to the drawings in detail, and particularly to FIG. 1, a preferred embodiment of an end effector, as further described below, extending from a catheter 70 of a surgical system 10 is shown forming holes or channels 12 (shown in phantom) in a heart 14 of a patient. The catheter 70 of the surgical system 10 is routed through the vascular system of the patient to a position near the inner ventricle wall 16 of the heart 14. The catheter 70 may be inserted into a femoral artery and guided through the aorta into the left ventricle of the heart, or the catheter 70 may be inserted into the femoral vein and advanced to the right side of the heart where the catheter 70 enters the left ventricle transeptically. The catheter 70 may include fiber optics (not shown) to allow a user or surgeon to view and monitor the procedure. Alternatively, the catheter 70 may be viewed by ultrasound imaging or fluoroscopic imaging.

Once the end effector is near the inner wall 16 of the heart 14, the surgical system 10 is activated and the distal end of the end effector is placed in contact with the inner wall 16 to transfer ultrasonic energy to the tissue. As the end effector advances or tunnels through the inner wall 16 of the heart 14, the end effector creates a channel 12 therethrough. The channel 12 provides a path for blood to flow into the myocardium 18 of the heart 14 from the heart cavity 20. It is contemplated that the end effector of the surgical system 10 may also create channels in other areas of the heart 14 as well as other tissue of a patient.

Figure 2:
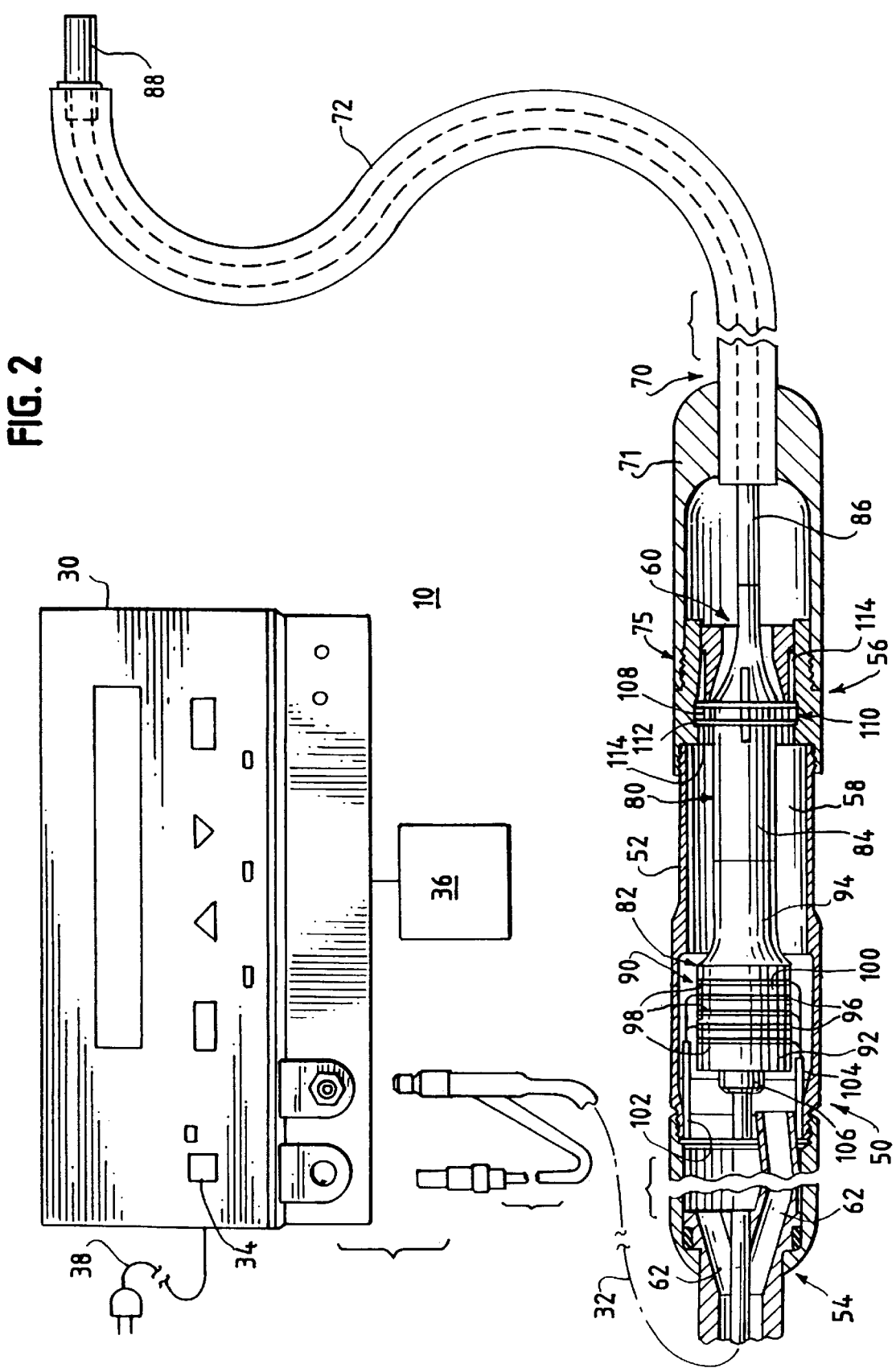
FIG. 2 is a partially broken away view and in partial cross-section of a preferred embodiment of an surgical system made in accordance with the present invention.

Referring now to FIG. 2, a preferred embodiment of the surgical system 10 is illustrated. The surgical system 10 generally includes a generator 30, a handpiece assembly 50, and an acoustic or transmission assembly 80. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. The end effector at the distal end of the acoustic assembly 80 is placed in contact with tissue of the patient to transfer the ultrasonic energy to the tissue. The cells of tissue in contact with the end effector of the acoustic assembly 80 will move with the end effector and vibrate.

As the end effector couples with the tissue, thermal energy or heat is generated as a result of internal cellular friction with the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector, the amount of pressure applied by the user, and the sharpness of the end effector. The end effector of the acoustic assembly 80 in the surgical system 10 tends to focus the vibrational energy of the system onto tissue in contact with the end effector, intensifying and localizing thermal and mechanical energy delivery.

As illustrated in FIG. 2, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase lock loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electric current supplied to the acoustic assembly 80 at a preselected constant level in order to achieve substantially constant vibrational amplitude at the end effector of the acoustic assembly 80. The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector may be controlled by, for example, controlling the amplitude of the electrical signal applied to the transduction portion 90 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord 38. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GENO1, available from Ethicon Endo-Surgery, Inc.

Referring still to FIG. 2, the handpiece assembly 50 includes a multi-piece housing or outer casing 52 adapted to isolate the operator from vibration of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. liquid crystal polymer (LCP), nylon, or polycarbonate). A suitable handpiece assembly is Model No. HP050, available from Ethicon Endo-Surgery, Inc.

Referring still to FIG. 2, the handpiece assembly 50 generally includes a proximal end 54, a distal end 56 and a centrally disposed axial opening or cavity 58 extending longitudinally therein. The distal end 56 of the handpiece assembly 50 includes an opening 60 configured to allow the acoustic assembly 80 of the surgical system 10 to extend therethrough. The distal end 56 of the handpiece assembly 50 is also coupled to a catheter 70, and the proximal end 54 of the handpiece assembly 50 is coupled to the generator 30 by a cable 32. The cable 32 may include air ducts or vents 62 to allow air to be introduced into the handpiece assembly 50 to cool the transducer assembly 82 of the acoustic assembly 80.

The catheter 70 generally includes an adapter 71 and an elongated flexible catheter body 72. The adapter 71 is coupled to the distal end of the handpiece assembly 50 by a threaded connection 75. It is contemplated that the adapter 71 may be attached to the handpiece assembly 50 by any suitable means.

The catheter body 72 of the catheter 70 has a proximal end, a distal end, and centrally disposed lumen extending longitudinally therethrough. The catheter body 72 may be made from a variety of materials including polyurethane, silicon rubber, or any other suitable material commonly used in conventional catheters. The catheter 70 is configured to permit the catheter body 72 to be inserted into the vascular system of a patient from an entrance site, e.g. a femoral artery or vein, once inserted, the catheter would be guided, for example, to the left ventricle of a heart 14 of a patient.

A guide wire may be inserted in a guide wire passage so that the guide wire may be longitudinally advanced or retracted through the distal end of the catheter body 72. A fluid lumen may also extend through the catheter body 72 to transmit a flushing fluid or to apply suction to the distal end of the catheter body 72 to clear fluids and debris from an area adjacent to the distal end.

Referring still to FIG. 2, the acoustic assembly 80 generally includes a transducer stack or assembly 82, a mounting device 84, a flexible transmission rod or wire 86, and an end effector or applicator 88. The transducer assembly 82, mounting device 84, transmission rod 86, and end effector 88 may be acoustically tuned such that the length of each component is an integral number of one-half system wavelengths ($N\lambda/2$) where the system wavelength $\lambda$ is the wavelength of a preselected or operating longitudinal vibration frequency f of the acoustic assembly 80. It is also contemplated that the acoustic assembly 80 may incorporate any suitable arrangement of acoustic elements. For example, the acoustic system 80 may comprise a transducer assembly 82 and an end effector 88 (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic system 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda/4$).

As shown in FIG. 2, the transducer assembly 82 of the acoustic assembly 80, which is known as a "Langevin stack," generally includes a transduction portion 90, a first resonator 92, and a second resonator 94. The transducer assembly 82 is preferably an integral number of one-half system wavelengths ($N\lambda/2$) in length. It is to be understood that the present invention may be alternatively configured to include a transducer assembly 82 comprising a magnetostrictive, electromagnetic, or electrostatic transducer.

The distal end the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density of material and modulus of elasticity used in the resonators 92 and 94, and the fundamental frequency of the transducer assembly 82. The second resonator 94 may be tapered inwardly from its proximal end to its distal end to amplify the ultrasonic energy vibrational amplitude.

The transduction portion 90 of the transducer assembly 82 preferably comprises a piezoelectric section of alternating positive electrodes 96 and negative electrodes 98, with piezoelectric elements 100 between the electrodes 96 and 98. The piezoelectric elements 100 may be fabricated from any suitable material, such as lead-zirconate-titanate, lead meta-niobate, lead titanate, or other ceramic piezoelectric crystal material. Each of the positive electrodes 96, negative electrodes 98, and piezoelectric elements 100 may have a bore extending through the center. The positive and negative electrodes 96 and 98 are electrically coupled to wires 102 and 104, respectively. The wires 102 and 104 transmit electrical signals from the generator 30 to the electrodes 96 and 98.

As shown in FIG. 2, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bore of the first resonator 92 and the bores in the electrodes 96 and 98 and piezoelectric elements 100. The threaded distal end of bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic system 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an antinode. (For purposes of this disclosure, the term "near" is defined as "exactly at" or "in close proximity to.") It is also contemplated that the mounting device 84 may be attached to the second resonator 94 by any suitable means, and that the second resonator 94 and mounting device 84 may be formed as a single or unitary component.

As illustrated in FIG. 2, the mounting device 84 is also coupled to the housing 52 near a node. The mounting device 84 may also include an integral ring 108 disposed around its periphery. The integral ring 108 is preferably disposed in an annular groove 110 formed in the housing 52 of the handpiece assembly 50 to couple the mounting device 84 to the housing 52. A compliant member or material 112, such as a pair of silicone O-rings attached by standoffs, may be placed between the annular groove 110 of the housing 52 and the integral ring 108 of the mounting device 84 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 may be configured to amplify the ultrasonic vibrational amplitude that is transmitted through the acoustic assembly 80 to the distal end of the end effector 88. In one preferred embodiment, the mounting device 84 preferably comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as a stepped horn, a conical horn, an exponential horn, or the like.

The distal end of the mounting device 84 may be coupled to the proximal end of the transmission rod 86 by an internal threaded connection. It is contemplated that the transmission rod 86 be attached to the mounting device 84 by any suitable means. The mounting device 84 is preferably coupled to the transmission rod 86 near an antinode.

As shown in FIG. 2, the transmission rod 86 extends longitudinally through a lumen of the catheter body 72. The distal end of the transmission rod 86 is preferably coupled to the proximal end of the end effector 88 by an internal threaded connection near an antinode. It is contemplated that the end effector 88 may be attached to the transmission rod 86 by any suitable means. Although the end effector 88 is shown as detachable from the transmission rod 86, it is also contemplated that the end effector 88 and transmission rod 86 may be formed as a single integral unit.

The transmission rod 86 and end effector 88 of the surgical system 10 are preferably made from a solid core shaft constructed of material, such as a titanium alloy (i.e., Ti-6Al-4V) or an aluminum alloy, which propagates ultrasonic energy efficiently. The transmission rod 86 and end effector 88 may be fabricated from any suitable material. It is also contemplated that the end effector 88 may have a surface treatment to improve the delivery of energy and desired tissue effect. For example, the end effector 88 may be micro-finished, coated, plated, etched, grit-blasted, roughened or scored to increase surface friction in order to enhance coagulation in tissue. The end effector 88 may also have a distal section having smaller cross-section area than a proximal section forming a vibrational amplitude step-up junction. When the transducer assembly 82 is energized, the distal end of the end effector 88 is configured to move longitudinally in the range of, for example, approximately 10 to 500 microns peak-to-peak and preferably in the range of about 30 to 100 microns at a predetermined vibrational rate and most preferably at about 90 microns.

The transmission rod 86 and end effector 88 may, for example, each have a length substantially equal to an integral number of half wavelengths (Nλ/2). In one embodiment, the transmission rod 86 has a diameter in the range of about 0.5–1 mm and the end effector 88 has a diameter in the range of about 0.1 mm–5 mm. The transmission rod 86 preferably has a diameter of 0.5 mm and the end effector 88 preferably has a diameter of about 0.5 mm–2 mm. Most preferably, the transmission rod 86 has a diameter of 0.5 mm and the end effector 88 has a diameter of about 1 mm. It is also contemplated that the transmission rod 86 and end effector 88 may be any suitable diameter.

Referring now to FIGS. 3–9, a number of preferred embodiments of an end effector (previously designated by number 88) for creating channels 12 in a heart 14 of a patient are illustrated. The end effector generally includes a channel creating tip or distal end. The tip of the end effector may be used to channel or burrow through the tissue of a heart of a patient when the end effector is energized. As those skilled in the art will appreciate, blunt and flat tips may tend to create more coagulation and hemostasis than pointed tips because of slower penetration.

As shown in FIG. 3, the tip 150a of the end effector 150 has a substantially round configuration. With this arrangement, the tip 150a of the end effector 150 can create channels in the heart of a patient while minimizing trauma, tissue damage, and cutting. In FIG. 4, the tip 152a of the end effector 152 has a substantially pointed or conical shape. With this configuration, the tip 152a can be utilized to minimize trauma and allow for easier tissue penetration when creating channels in the heart of the patient. In FIG. 5, the tip 154a of the end effector 154 has a substantially blunt, flat, or square configuration. With this embodiment, the tip 154a of the end effector 154 can minimize tissue displacement and maximize tissue cutting and removal when creating channels in the heart of the patient. In FIG. 6, the tip 156a of the end effector 156 has a substantially beveled or tapered configuration. The edges at the juncture of the sides of the tapered section of the tip 156a provide narrow cutting edges and the broad surfaces therebetween increase the amount of energy delivered by the edges to increase coagulation or hemostasis.

Referring now to FIG. 7, the tip 158a of the end effector 158 has a substantially pyramidal configuration or triangular cross-section. The edges at the juncture of the sides of the triangular-shaped tip 158a provide narrow cutting edges to facilitate penetration and advancement, while the broad surfaces therebetween afford coagulation surfaces when creating channel in the heart of the patient. In FIG. 8, the tip 160a of the end effector 160 has multiple steps 162 to maximize tissue removal when creating channels in the heart of the patient. In FIG. 9, the tip 164a of the end effector 164 has a stepped shoulder 166 having any suitable shaped end 168. The stepped shoulder 166 can be used as a indicator of penetration depth and to prevent over insertion. The stepped shoulder 166 preferably provides additional amplification of the ultrasonic vibration and amplitude to increase cutting. A stepped shoulder such as 166 may be employed in conjunction with any of the end effectors illustrated in FIGS. 3–11 or in any other suitable end effector.

Referring now to FIG. 10, the tip 170a of the end effector 170 has a hollow tubular end to core out tissue. Hollow lumen 170b may also be used to irrigate or aspirate tissue. In FIG. 11, the distal end 172a of the end effector 172 has a larger diameter than a shaft 174 to promote a constant diameter channel and to prevent formation of channels having cone-shaped cross-sections. It is also contemplated that the end effector of the surgical system 10 may also be stepped or tapered inwardly or have a receding diameter.

The use of the surgical system 10 will now be described with reference to FIGS. 1 and 2. Initially, the surgical system 10 is connected to the generator 30 in an unarmed state. The generator 30 then measures the initial parameters of the acoustic assembly 80 and arms the system. The surgical system 10 is then in a ready state, at which point the surgeon may position the catheter at the desired site within the body and then trigger the generator 30 using the triggering mechanism 36.

In one method of treating a patient, the catheter body 72 of the handpiece assembly 50 is inserted into a vein or artery in a cardiovascular system of a patient. The catheter 70 is manipulated through the vessel of a patient into, for example, the left ventricle of the heart 14 of a patient until the distal end of the end effector 88 reaches a desired location. The catheter body 72 may be inserted into a femoral artery and advanced through the aorta into the left ventricle via the aortic valve. Alternatively, the catheter 70 may be inserted into the femoral vein and advanced to the right side of the heart where the catheter 70 enters the left ventricle transeptically. The catheter 70 may use a guide wire to guide the catheter through the cardiovascular system of the patient to the desired treatment area. The catheter 70 may also be visually monitored by the physician using fiber optics or may be viewed by ultrasound imaging or fluoroscopic imaging.

Once the end effector 88 is properly positioned near the inner wall 16 of the heart 14, the user may activate the generator 30 to cause the end effector 88 to vibrate. The distal end of the end effector 88 may then be advanced to tunnel or burrow through the inner wall 16 of the heart 14 to form a channel 12 into the myocardium 18 of the heart 14. As the distal end of the end effector 88 contacts tissue and couples vibrational energy to the tissue, heat is generated in the tissue to break protein hydrogen bonds, causing the highly structured protein to denature. The energized distal end of the end effector 88 generates thermal energy, mechanical pressure, and cavitation in the tissue which causes the end effector 88 to penetrate the tissue and create channels in the wall of the heart. After the end effector is advanced a desired distance into the inner wall, the end effector 88 is then withdrawn. In the present method, the distal end of the end effector 88 preferably does not penetrate through the outer wall of the heart.

A plurality of channels may be formed through the inner wall 16 of the ventricle chamber and into the myocardium 18. Preferably, the channels are approximately 1 mm in diameter. These channels provide a flow path for blood into the myocardium 18 from the ventricular chamber 20. It is contemplated that any suitably sized diameter may be formed through the inner wall 16 without departing from the spirit and scope of the present invention.

Figure 12:
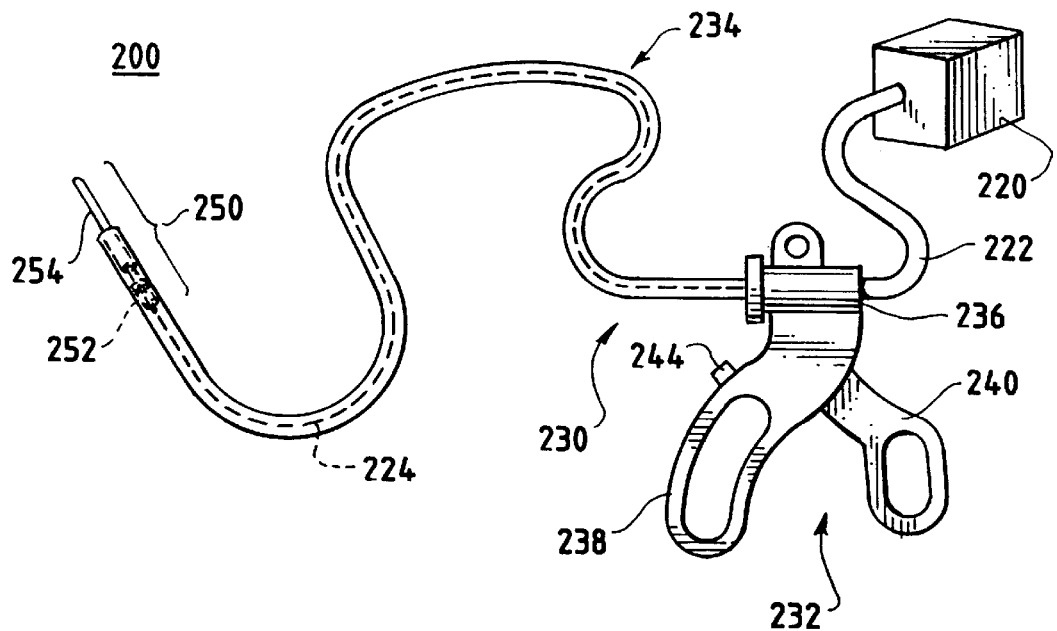
FIG. 12 is a perspective view of another preferred embodiment of an surgical system according to the present invention.

Referring now to FIG. 12, another preferred embodiment of the surgical system 200 is illustrated. The surgical system 200 operates and may be used in the same general manner to create channels in the inner wall of the heart as described above. The surgical system 200 generally includes a generator 220, a probe or catheter assembly 230, and an acoustic assembly 250. The generator 220 is substantially similar to the generator described above. As such, further description of the generator 220 is unnecessary for a complete understanding of present invention.

The probe assembly 230 generally includes a handle 232 and a catheter body 234. The handle 232 is configured to allow it to be easily grasped and held by a physician in order to allow the catheter body 234 to be manipulated within the patient. The handle 232 preferably includes a housing 236, a finger grip 238, a thumb grip 240, and a triggering mechanism. The distal end of the housing 236 is coupled to the catheter body 234 of the probe assembly 230 and the proximal end of the housing 236 is coupled to the generator 220 by a cable 222.

The housing 236, finger grip 238, and thumb grip 240 are preferably constructed from a durable plastic, such as Ultem®. It is also contemplated that these components may be made from a variety of materials including other plastics (i.e. liquid crystal polymer (LCP), nylon, or polycarbonate).

In one embodiment, a switch 244 may be incorporated into the finger grip 238 of the handle 234 to allow the generator 220 to be activated by a user. Alternatively, the triggering mechanism may comprise a foot activating switch that is detachably coupled or attached to the generator 220 by a cable or cord to allow a user or surgeon to activate the generator 220.

The catheter body 234 of the probe assembly 230 has a proximal end, a distal end, and centrally disposed lumen extending longitudinally therethrough. The catheter body 234 may be made from a variety of materials including polyurethane, silicone rubber, or any other suitable material commonly used in conventional catheters. The catheter body 234 is configured to be inserted into the vascular system of a patient from an entrance site, e.g. a femoral artery or vein, once inserted, the catheter would be guided, for example, to the left ventricle of a heart of a patient.

A guide wire may be inserted in a guide wire passage so that the guide wire may be longitudinally advanced or retracted through the distal end of the catheter body 234. A fluid lumen may also extend through the catheter body 234 to transmit a flushing fluid or to apply suction to the distal end of the catheter body 234 to clear fluids and debris from an area adjacent to the distal end.

Figure 13:
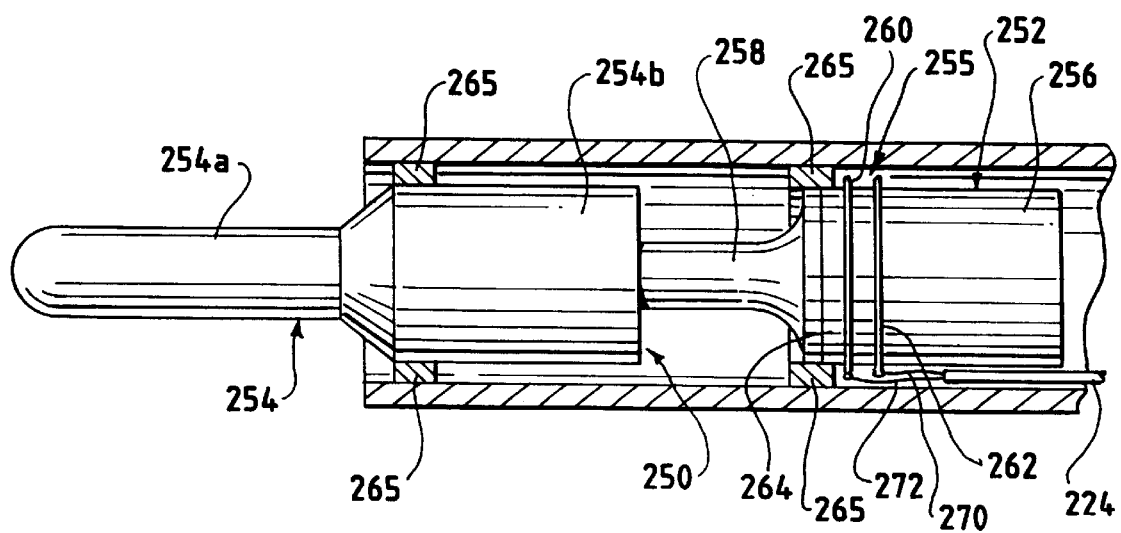
FIG. 13 is a view partially broken away, cross-sectional view of the acoustic assembly of the surgical system of FIG. 12.

Referring now to FIG. 13, a preferred embodiment of the acoustic assembly 250 of the surgical system 200 is illustrated. The acoustic assembly 250 is preferably disposed near the distal end of the catheter body 234. The acoustic assembly 250 generally includes a transducer stack or assembly 252 and an end effector or applicator 254.

The transducer assembly 252 of the acoustic assembly 250 generally includes a transduction portion 255, a first resonator 256, and a second resonator 258. The transducer assembly 252 is preferably an integral number of one-half system wavelengths (Nλ/2) in length. It is also contemplated that the acoustic assembly 250 may be any suitable arrangement of acoustic elements. For example, the acoustic assembly 250 may comprise a transducer assembly, a mounting device, a transmission rod, and an end effector as described above. It is to be understood that the present invention may be alternatively configured to include a transducer assembly comprising a magnetostrictive, electromagnetic or electrostatic transducer.

The distal end of the first resonator 256 is connected to the proximal end of transduction portion 255, and the proximal end of the second resonator 258 is connected to the distal end of transduction portion 255. The first and second resonators 256 and 258 are preferably fabricated from titanium, aluminum, steel, or any other suitable material. The second resonator 258 is preferably tapered inwardly from its proximal end to its distal end to amplify the ultrasonic vibration amplitude.

The transduction portion 255 of the transducer assembly 252 preferably comprises a piezoelectric section of one or more alternating positive electrodes 260 and to negative electrodes 262, with piezoelectric elements 264 alternating between the electrodes 262 and 264. The piezoelectric elements 264 may be fabricated from any suitable material, such as lead-zirconate-titanate, lead meta-niobate, lead titanate, or other ceramic piezoelectric crystal material. The piezoelectric elements 264 are energized in response to the electrical signal supplied from the generator 220 to produce an acoustic standing wave in the acoustic assembly 250 as described above.

The transducer assembly 252 is operatively coupled to the generator 220 via a cable 224 enclosing one or more wires 270 and 272. The wires 270 and 272 are connected to positive electrodes 260 and negative electrodes 262, respectively. The transducer assembly 252 is substantially similar to the transducer assembly described above except that it is reduced in size. As such, further description of the transducer assembly 252 is unnecessary for a complete understanding of the invention. It is to be also understood that the present invention may be alternatively configured to include a transducer assembly 252 comprising a magnetostrictive, electromagnetic, or electrostatic transducer.

The end effector 254 of the acoustic assembly 250 has a proximal end, a distal end, and may have a length substantially equal to an integral number of one-half system wavelengths (Nλ/2). The proximal end of the end effector 254 is preferably coupled to the distal end of the second resonator 258 by an internal threaded connection near an antinode. It is also contemplated that the end effector 254 may be attached to the second resonator 258 by any suitable means, and that the second resonator 258 and end effector 254 may be formed as a single or unitary component.

As shown in FIG. 13, the end effector 254 preferably has a distal region 254a having a smaller cross-section area than a proximal region 254b thereof, thereby forming a vibrational amplitude step-up junction 254c. The step-up junction 254c acts as a velocity transformer as known in the art, increasing the magnitude of the ultrasonic vibration transmitted from the proximal region 254a to the distal region 254b of the end effector 254. The end effector 254 is preferably fabricated from a titanium alloy, such as Ti-6Al-4V. It is contemplated that the end effector 254 may be manufactured from any suitable material without departing from the spirit and scope of the invention.

The end effector 254 may preferably have a length of an integral multiple of half wavelengths (Nλ/2) in order to produce the maximum longitudinal deflection at its remote end. The end effector 254 has a diameter of about 0.1–5 mm, and preferably a diameter of about 0.5–2 mm, and most preferably a diameter of 1 mm. The end effector 254 may have any suitable configuration, such as the arrangements shown in FIGS. 3–11 as described above.

As shown in FIG. 13, a plurality of seals 265 are distributed along the lumen of the catheter body 234 to support the transducer assembly 252. The seals 265 are preferably fabricated from silicone to isolate the catheter body 234 from the transducer a assembly 252. As those skilled in the art will recognize, the transducer assembly 252 or acoustic assembly 250 may be supported by any suitable means. It is also contemplated that the catheter body 234 may be configured to attach to a housing that holds the transducer assembly 252. For example, a housing may be mounted at or near the distal end of the catheter body 234. Alternatively, the catheter body 234 may have a first section and a second section with a housing disposed therebetween to support the transducer assembly.

The devices and methods of the present invention allow channels to be formed in the inner wall of the heart to enhance the flow of blood to the heart muscle in order to improve various types of heart disease. The channels allow entry of reviving, oxygen-rich blood to pass from the ventricle chamber into the myocardium of the heart.

The devices in accordance with the present invention may be inserted into the vascular system of a patient to allow access to an area in need of increased blood circulation due to heart disease. The devices and methods of the present invention may be useful for those too sick for bypass surgery.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. A surgical device for creating channels in tissue comprising:
    a transducer assembly disposed within a catheter body adapted to vibrate at an ultrasonic frequency in response to electrical energy; and
    an end effector extending from the catheter body, the end effector including means adapted to receive the ultrasonic vibrations from the transducer assembly and transmit the vibrations to the distal end of the end effector, wherein the end effector has a channel forming tip configured to form channels in.

2. The device of claim 1 further comprising a mounting device having a first end and a second end, the mounting device being adapted to receive ultrasonic vibration from the transducer assembly and to transmit the ultrasonic vibration from the first end to the second end of the mounting device.

3. The device of claim 2 wherein the mounting device has a length which is substantially equal to an integral multiple of one-half wavelengths of the ultrasonic frequency.

4. The device of claim 1 further comprising a flexible transmission rod having a first end and a second end, the transmission rod adapted to receive and to transmit the ultrasonic vibration from the first end to the second end of the transmission rod.

5. The device of claim 4 wherein the transmission rod has a length which is substantially equal to an integral multiple of one-half wavelength of the ultrasonic frequency.

6. A surgical device for creating channels in tissue of a patient comprising:
    a catheter defining a lumen;
    a transducer assembly disposed within the catheter and along a lengthwise dimension of the catheter; and
    an end effector operatively coupled to the transducer assembly and extending distally relative to the transducer assembly, the end effector having a vibrating channel-forming tip configured to create channels in the heart of a patient.

7. The device of claim 6 wherein the device is configured to create substantially constant diameter channels.

8. A surgical device comprising:
    a tubular catheter body having a first end, a second end and a lumen extending longitudinally therethrough, the catheter body configured to be placed within a vessel of a patient's vascular system;
    a non-optical end erector extending from the second end of the catheter, the end effector having a channel forming tip configured to create channels in selected tissue of a patient; and
    a transducer assembly disposed within the catheter and adapted to generate ultrasonic energy in response to electrical energy to vibrate the end effector.

9. The device of claim 8 wherein the transducer assembly includes one of a piezoceramic, magnetostrictive, electromagnetic, and electrostatic transducer assembly.

10. The device of claim 8 wherein the end effector includes a tip from the class containing a flat tip, a pointed tip, a tapered tip, a triangular tip, a hollow tabular tip, a hollow tubular tip, a cylindrically shaped tip and a cylindrical channel-forming tip.

11. The device of claim 8 wherein the end effector includes a first portion and a second portion, the second portion extending from the first portion and having a smaller diameter than the first portion.

12. The device of claim 11 wherein the end effector includes a third portion extending from the second portion and having a smaller diameter than the second portion.

13. A surgical device comprising:
    a catheter comprising an ultrasonic transducer element and an end effector, wherein the ultrasonic transducer is disposed within the catheter;
    the end effector having a channel forming tip configured to form channels in selected tissue of a patient; and
    the tip adapted to vibrate at a selected frequency, the tip chosen from a group consisting of a cylindrical tip, a triangular tip, a round tip, a tapered tip, a conical tip, a square tip, a tip having multiple steps, and a tip having a stepped shoulder.

* * * * *